United States Patent [19]

Fox

[11] Patent Number: 5,041,266
[45] Date of Patent: Aug. 20, 1991

[54] TRAY FOR IMMUNOMETRIC DETERMINATIONS

[75] Inventor: William A. Fox, Burlington, N.C.

[73] Assignee: Hoffmann-La Roche Inc., Nutley, N.J.

[21] Appl. No.: 454,587

[22] Filed: Dec. 21, 1989

[51] Int. Cl.⁵ .................. G01N 31/00; G01N 33/545
[52] U.S. Cl. ...................................... 422/102; 422/57; 422/58; 422/73; 422/99; 422/104; 422/906; 422/907; 435/301; 436/531; 436/535
[58] Field of Search .................. 422/57, 58, 73, 99, 422/102, 104, 906, 907; 436/531, 535; 435/301

[56]     References Cited
U.S. PATENT DOCUMENTS 4,314,026  2/1982  Descamps-Latscha .......... 422/52 X
4,468,371  8/1984  Chen et al. ....................... 422/102
4,599,315  7/1986  Terasaki et al. ................. 422/73 X
4,628,026 12/1986  Gardell et al. ................. 436/519 X
4,735,778  4/1988  Maruyama et al. .............. 422/102
4,770,856  9/1988  Uthemann et al. ............ 422/102 X Primary Examiner—Robert J. Warden
Assistant Examiner—Stephanie Blythe
Attorney, Agent, or Firm—George M. Gould; Bernard S. Leon; William H. Epstein

[57]     ABSTRACT

A microtiter plate containing a plurality of reaction wells for conducting immunogenic reactions wherein the bottom wall of the reaction well has an inner surface which is substantially hydrophilic, and the side wall of the reaction well has an inner surface which is substantially hydrophobic and a process for producing said trays.

2 Claims, 4 Drawing Sheets

TRAY FOR IMMUNOMETRIC DETERMINATIONS

BACKGROUND OF INVENTION

Immunogenic assays involving an antibody antigen reaction to detect an antibody or antigen in biological samples have been an important tool in the in vitro diagnosis of human diseases or disorders. In carrying out such immunogenic assay, microtiter plates or trays have become an important tool particularly in the detection of Human Leucocyte Antigen (HLA) as well as certain genetic information which may be present on the surface of nucleated cells, such as lymphocytes. This information is extremely useful in organ transplantation and parentage testing. Tissue typing assays have been standardized to promote accuracy as well as reproducibility of results. Part of this accepted standardization of the assay involves use of the "Terasaki" style microtiter tray set forth in U.S. Pat. No. 4,599,315, issued July 8, 1986. This is a small plastic tray (approximately 5 cm×7 cm) containing a number of reaction wells. Other types of microtiter trays or plates are disclosed in U.S. Pat. No. 4,735,778.

The standard plastic microtiter tray is made of a light transmitting hydrophobic polymer such as polystyrene. It is important that the plate be formed from a light transmitting polymer since reading of the wells occurs through use of their light transmitting properties. In order that the antisera and reagents necessary for a diagnostic assay spread evenly into the bottom of the reaction well when the loaded, it is necessary to treat the plastic surface to make it wettable. This is usually done, as disclosed in Akerman, et al., PCT International Application WO87/02619, May 7, 1987 by oxidizing the inner surface of the reaction wells by conventional electrode discharge devices such as a corona discharge. Without this treatment the drops of fluid would remain soneroid, as a drop of water on wax paper. In the past, the entire plastic tray is treated or oxidized as it passes under an electrode assembly on a conveyor mechanism. By this process the surface which undergoes the oxidation treatment includes the surface of the bottom of the well, as well as the surface of the side wall of the wells. We have found this to be undesirable since antiserum (reagent) and/or cell (sample) microdrops are not accurately delivered to the center of the well. In fact, these liquid drops fall on a side wall of the well and adhere. In this manner, the liquids for carrying out an immunoassay do not reach the bottom of the well where they should meet and mix with a suitable component (sample or reagent) in order that the immunogenic reaction can take place.

We have found that the poor mixing and adherence to the side walls is troublesome in using this microtiter plates. It is difficult to direct the very small microdrops (1 microliter) exactly to the center of the well at each time, as ideally it should. Everytime a microdrop is inaccurately delivered so that it adheres to a side wall of a well, and this is noticed by the technician who carries out the assay, the technician should properly try to make sure that the cells to be tested get properly mixed with with the antiserum at the bottom of the reaction well. For this purpose he may have to use a stirring wire and/or carry out a centrifugation of the tray.

Unfortunately, since the microdrops (antiserum or cells) are so small, not every inaccurate delivery thereof to a side wall of the well is noticed and corrected by necessary mixing operation carried out by the technician. Thus when such inaccurate delivery of the microdrops takes place and remains unnoticed, the cells under test and the antiserum are not mixed with each other and a false negative reaction results. It is therefore highly desirable to overcome this difficulty in order to improve the reliability of the assays.

SUMMARY OF THE INVENTION

According this invention the above mentioned difficulty is overcome with a tray wherein the bottom wall of the reaction well has an inner surface which is substantially hydrophilic, and the side wall of the reaction well has an inner surface which is substantially hydrophobic. A preferred embodiment of the tray according to the invention is characterized in that the inner surface of the bottom wall of the reaction well has been made hydrophilic by selectively exposing said surface to an oxidation process.

In an alternative embodiment of the tray according to the invention the inner surface of the bottom wall of the reaction wells can be coated with an hydrophilic layer while the side walls remain hydrophobic.

In a further preferred embodiment of the tray according to the invention as described above, the reaction wells contain reagents, i.e. the reagents are pre-filled into the reaction wells to perform the tray so that the user only need add the sample to be tested to the reagents already present in the reaction well. The reagent contained in the reaction well is preferably covered by a suitable liquid which prevents evaporation of the reagent, but which is permeable for the sample to pass through and reach the pre-filled reagent present in the reaction well.

According to a second aspect of the invention the new and advantageous properties of the tray according to the invention are obtained with a method for treating a tray for carrying out immunogenic reactions to analyze biological samples, said tray comprising a plurality of reaction wells adapted to receive a biological sample, each reaction well having a bottom wall and a side wall. The method for producing the tray of this invention is carried out by selectively exposing the inner surface of the bottom of the reaction well to a surface oxidation process. In this manner the surface of the bottom wall is rendered hydrophilic. At the same time this oxidation is carried out the inner surface of the side wall of the reaction well is excluded from this or any other surface oxidation process.

The main advantages obtained with a tray and a method according to the invention are as follows:

the possibility of the false negative reactions due to non-mixing of the sample with the reagent is substantially reduced, the amount of handling and of technicians work for carrying out the assays is also substantially reduced, because technicians do not have expend time searching for reaction wells where samples and reagents do not mix, or attempting to correct this with stirring wires or by centrifugating the trays.

BRIEF DESCRIPTION OF THE DRAWINGS

Preferred embodiments of the invention will now be explained in detail with reference to the enclosed drawings, in which.

DETAILED DESCRIPTION OF THE PREFERRED EMBODIMENTS

This invention provides a new and improved microtiter test apparatus for conducting an immunogenic reaction to analyze biological fluid samples for diagnostic purposes. By this procedure biological samples are generally analyzed for determining the presence and/or the amount of an antigen antibody component of an immunological reaction. The preferred component detected by the microtiter plate of this invention is Human Leukocyte Antigen (HLA). Determination of the presence of this antigen identifies certain genetic information which may be present on the surface of neuclated cells, such as lymphocytes. This information is extremely useful in the areas of organ transplantation and parentage testing.

In carrying out the antibody antigen assay, these microtiter trays are generally small plastic trays (approximately 5 cm × 7 cm) containing a plurality of reaction wells. In these assays, approximately 1 ml of the biological fluid to be detected is utilized for this assay. In addition, in order that the immunological reaction be carried out, various reagents are utilized, one of which contains the complementary component of the antibody or antigen to be detected. The complementary component is the other component which immunologically reacts with either the antibody or antigen to be detected in the biological fluid. Generally approximate 1 microliter of each of these reagents is loaded into each of the various wells in the microtiter plate.

Figure 1:
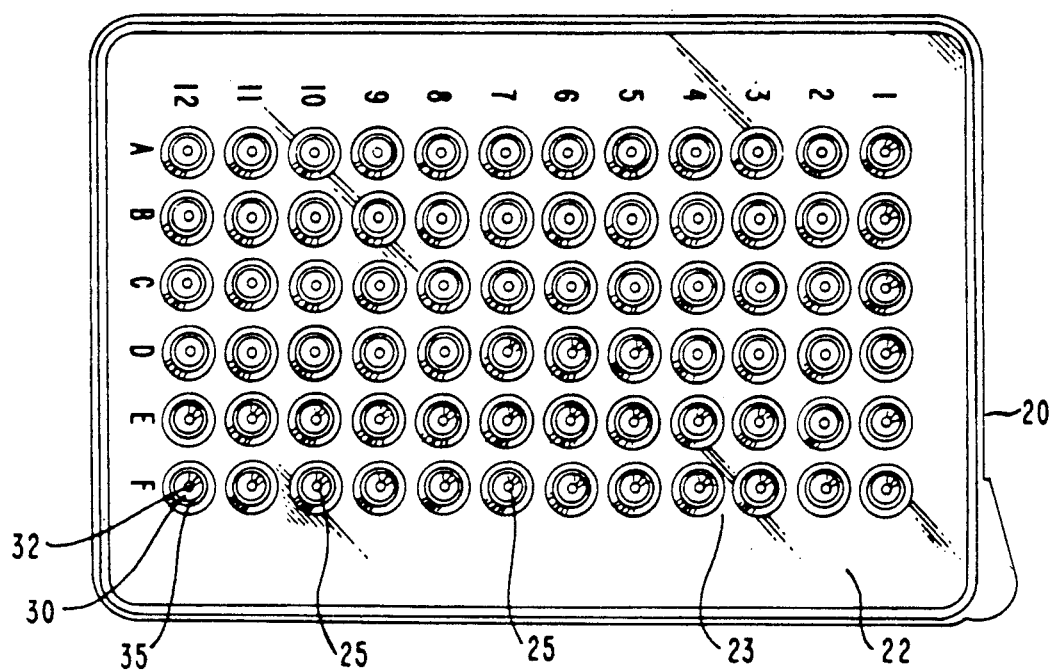
FIG. 1 is a top plan view of the tray according to this invention.
Figure 4:
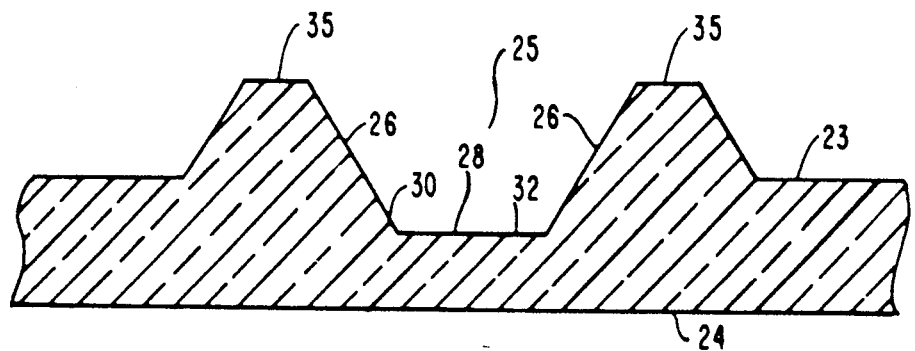
FIG. 4 is a section of the tray portion of FIG. 1 through one of the wells.

The improved microtiter test apparatus in accordance with the present invention is shown in FIG. 1, As shown in FIG. 1, the test apparatus 20 includes a plate member 22 having a top surface 23 and a bottom surface 24 [FIG. 4]. The tray is preferably made from a light transmitting plastic. Any conventional light transmitting material which is inert to the immunogenic reaction which takes place can generally be used in accordance with this invention. In accordance with the preferred embodiment of this invention, the plate member 22 is formed from a hydrophobic plastic such as polystyrene. The plate member 22 includes a plurality of spaced-apart wells 25. These wells 25 are configured and adapted to hold and receive a small titer of biological fluid for conducting the immunogenic reaction. In these wells 25 the immunogenic reaction between the reagents and the biological fluid to be analyzed takes place.

Each of the wells 25, as seen in FIG. 4, contain a side wall 26 and a bottom wall 28. The side wall 26 has an inner surface 30 and the bottom wall 28 has a inner surface 32. It is the inner surfaces of these walls which are adapted to retain the sample of biological fluid during the immunogenic reaction. The inner surfaces 30 of the side walls and the inner surfaces 32 of the bottom walls can be flat or curved to form a "U" shaped well. In accordance with this invention, the various spaced apart wells 25 are defined by the top surface 23 of the plate member 20. In accordance with the preferred embodiment of this invention, the wells 25 are within the top surface 23 of the plate member 22 while the bottom surface 24 of plate member 20 is flat and retains the bottom wall 28 of each of these wells. See FIGS. 1, 4 and 5. On the other hand, as an alternate embodiment, the top surface 23 of plate member 22 can form the bottom wall of the well 25. In this alternate embodiment, the wells 25 are raised above the surface 23 of plate member 22.

Figure 5:
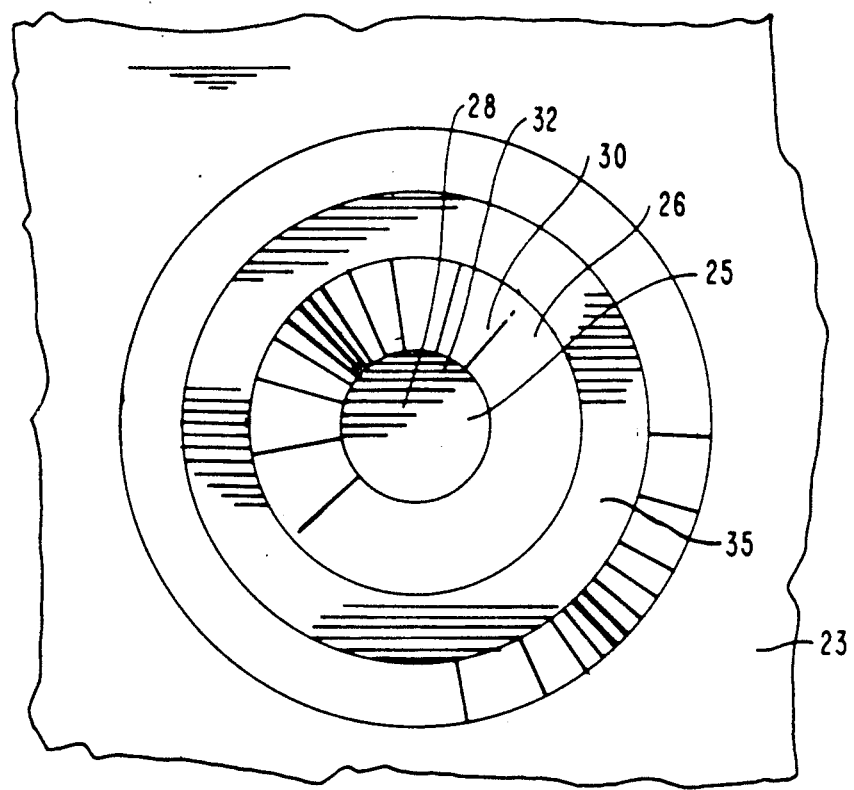
FIG. 5 is a top plan view of the tray portion through one of the wells of the tray of FIG. 1.

As best shown in FIGS. 1, 4 and 5, in accordance with a preferred embodiment of this invention, the microtiter wells 25 include an upper rim 35 which defines the opening of well 25. This opening has sufficient surface area to allow the introduction of the biological fluid sample and reagents into the microtiter well 25. Inner surface 30 extends between the upper rim 35 and the inner surface 32 of the bottom well 28. The surface area of the opening defined by rim 35 is greater than the surface area of the inner surface 32 of bottom wall 28. Therefore in accordance with a preferred embodiment of this invention, the side walls 26 and their inner surfaces 30 of the wells 25 are tapered inwardly towards the inner surface 32 of the bottom wall 28.

In accordance with this invention, the wells 25 are so constructed that the inner surface 32 of the bottom wall 28 is hydrophilic in nature, where as the inner surface 30 of side wall 26 is hydrophobic. In accordance with this invention, we have found that when the side walls of the wells of the microtiter plate are hydrophobic and the bottom surface is hydrophilic, the immunological reaction between the biological fluid to be tested and the reagents occur more efficiently. In accordance with this invention, the use of hydrophobic side walls in combination with the hydrophilic bottom wall of the well produces new and unexpected results allowing the reagents and fluid to spread evenly into the bottom of the reaction well when they are loaded on to the microtiter plate. This allows one to utilize very small amounts of the reagents and the biological fluid to produce maximum efficiency and results and avoiding false positive and more importantly false negative results. Previously the use of hydrophilic surfaces including the surfaces of the side walls can present problems especially when small amounts of reagents on all samples are used. Specifically the small amounts can accidentally touch the side of the wells when added. We have found that such aqueous reagents adhere to the side of the well instead of spreading across the well bottom as intended and necessary for carrying out immunological reactions. It has been found that by the provision of well with the side walls having hydrophihic inner surfaces, with the inner surfaces of the bottom wall being hrdrophilic, an even spread of the reagents and biological fluid sample occurs across the inner surface of the bottom wall so that immunological reactions will occur expeditiously even with very small amounts of reagents and biological fluids.

In accordance with this invention, any conventional method of rendering the inner surface 30 of the side wall 26 hydrophobic and the inner surface 32 of the bottom wall 28 hydrophilic can be utilized in accordance with this invention. One such method is by constructing the inner surfaces 30 of the side walls from a hydrophobic plastic and the inner surface 32 of the bottom wall 28 from a hydrophilic plastic. Generally this is tedious and cumbersome. On the other hand, one can coat the inner surface 30 with the hydrophobic material and the inner surface 32 with the hydrophilic material.

In accordance with the preferred embodiment of this invention, the tray 20 is formed from a hydrophobic plastic and all surfaces and walls of said tray 20 are formed from this hydrophobic plastic. For reading of these trays or plates, these trays or plates are formed from any conventional light transmiting polymer such as polystyrene. Generally these light transmitting polymers are hydrophobic in nature. The bottom walls of the wells of these trays are rendered hydrophilic by selectively exposing only the inner surface to oxidization by shielding the inner surface of said side walls. Any conventional method of selectively exposing the inner surface to oxidation while shielding the inner surface of said side walls can be utilized in accordance with this embodiment. Furthermore, any conventional method of oxidizing a hydrophobic plastic to a hydrophilic plastic can be utilized in accordance with this method. The preferred method of oxidizing is by treatment of the plastic of the inner surfaces of the bottom wall with electrons such as those discharged by an electron discharge means such as a corona discharge apparatus. A typical corona discharge apparatus is disclosed in European patent application 0,074,790 published Mar. 23, 1983 Landis.

Figure 2:
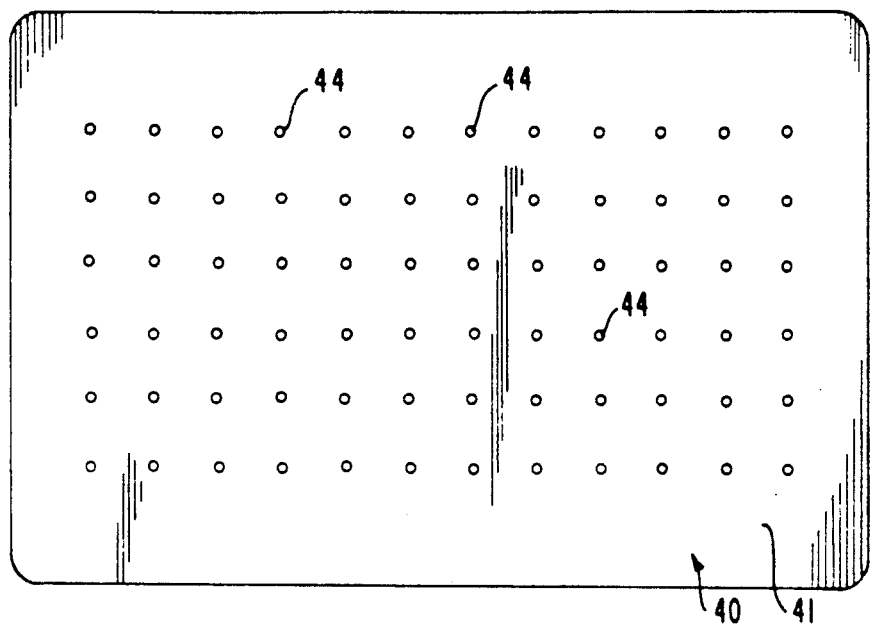
FIG. 2 is a top plan view of the shield.
Figure 3:
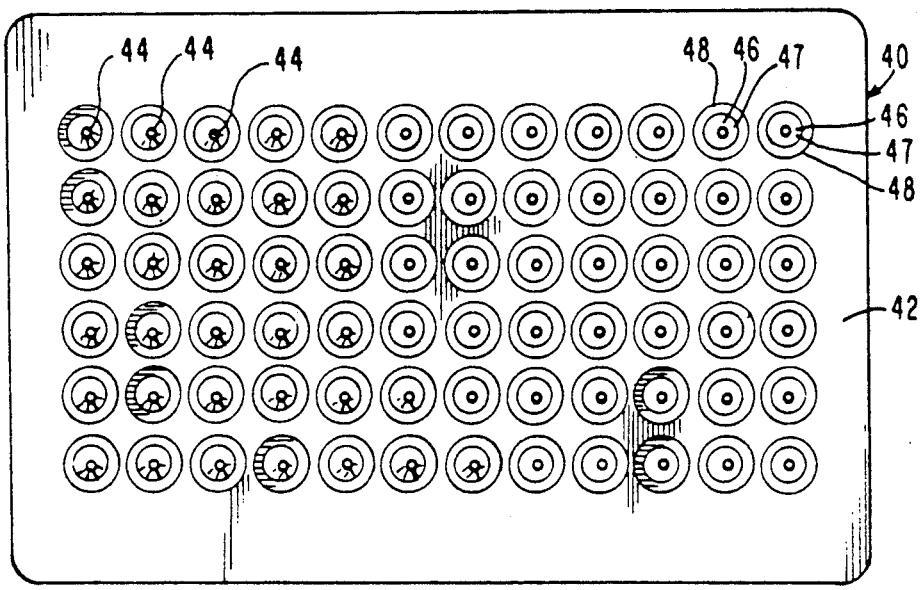
FIG. 3 is a bottom plan view of the shield.

Another aspect of this invention is to utilize an electron shield which can shield the inner surface 30 of the side wall 26 while allowing the inner surface 32 of the bottom wall 28 to be exposed to the electron discharge. In accordance with this embodiment, a shield is constructed as in FIG. 2. This shield constitutes a mat 40, the top surface 41 of which is illustrated in FIG. 2 and the bottom surface 42 is illustrated in FIG. 3. The bottom surface 41 contains a plurality of apertures 44 spaced throughout the shield 40. The shield 40 is so configured that the bottom surface 42 fits on the surface 23 of the plate 20 and the apertures 44 are so spaced within the mat 40 so that when the upper surface 41 of mat 40 is placed upon the top surface 23 of plate member 22, the apertures 44 coincide with the bottom walls 28 of said wells 25. The surface areas of each of the apertures 44 are so dimensioned that they have the same surface area as the inner surface 32 of the bottom wall 28 of the wells 25. In this manner the shield 40, through apertures 44, will allow the electrons discharged by the electrode discharged means to contact and treat the inner surface 32 of bottom wall 28. As shown in FIG. 3 especially in FIG. 6, the bottom surface 42 of mat 40 is configured that when its placed upon the wells the mat conforms to the inner surface 30 of side wall 26 with the openings in the apertures 44 conforming to the surface area of the inner surface 32 of bottom wall 28. As seen from FIG. 6, when the mat 40 is placed over plate 22, it shields the inner surface 30 of side walls 26.

Figure 6:
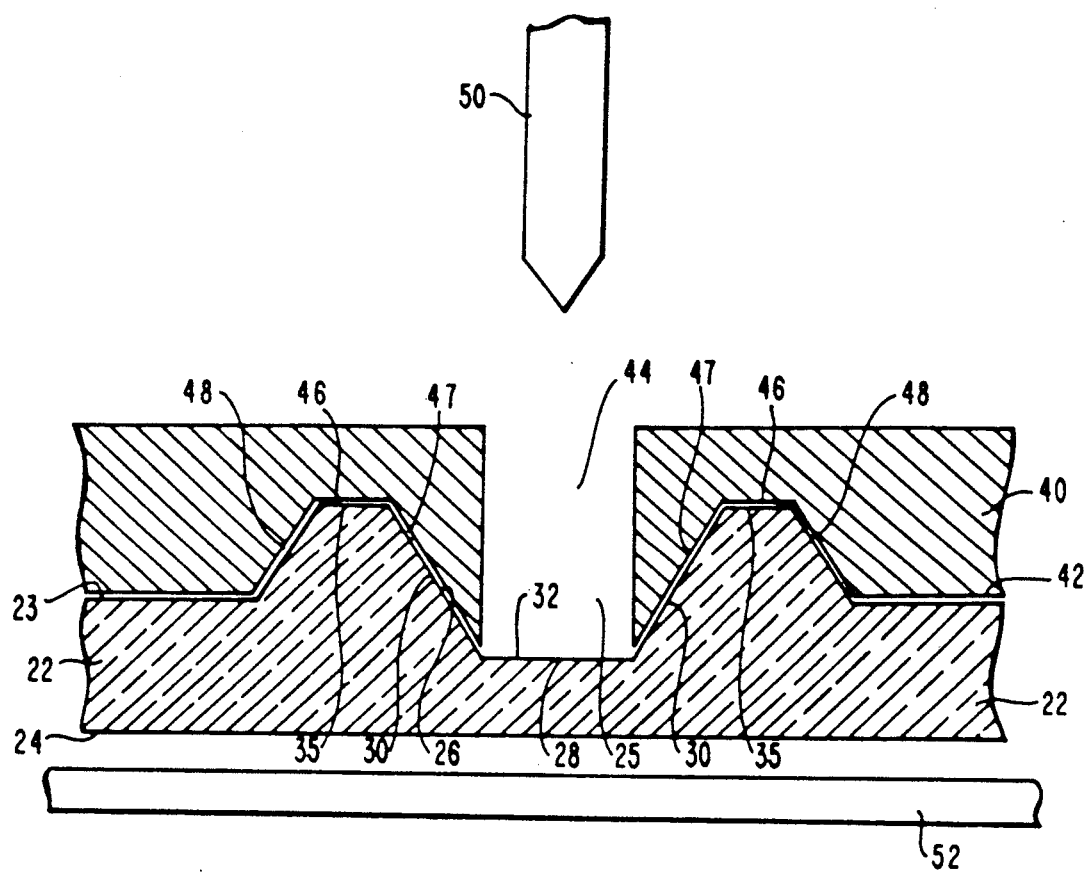
FIG. 6 is an assembled section of the shield of FIG. 2. and the tray of FIG. 1 through one of the wells of FIG. 1 during exposure to an oxidation source.

Referring to FIGS. 3 and 6, the apertures 44 in the bottom portion consists of an opening 46 between side wall 47 and 48. The opening 46 between side walls 47 and 48 is contoured to allow the rim 35 of plate 22 to fit within the opening 46. The side walls 47 and 48 of aperture 44 are so dimensioned that when the rim 35 engages the opening 46 of the mat 40, the walls 47 shields the entire inner surface 30 of side wall 26 of well 25. Walls 47 surround apertures 44 to provide a flange which projects to the inner surface 32 of the bottom wall 28 and covers the inner surface 30 of the side wall 26 to shield the side wall 26 from electron discharge. In this manner when an electrode 50 releases electrons, only the surface 32 of the bottom wall 28 will be treated by the electrons and oxidized to form a hydrophilic surface where as the surfaces 30 of side walls 26 will be shielded by the mat 40 by means of the engagement of the wall 47 of mat 40 with the inner surface 30 of side wall 26. In exposing the wells 25 of plate 22 to the electrode 50, the plate 22 is placed upon a conveyor belt 52. In this manner the plates and wells are moved into and out of engagement with the electrode discharge means 50.

The mat in accordance with this convention can be made from any conventional solid material impervious to electrons. Any conventional electron shield material can be utilized. Generally, it is preferred for economic reasons to use rubber, i.e. neoprene, as the shielding material.

Figure 7:
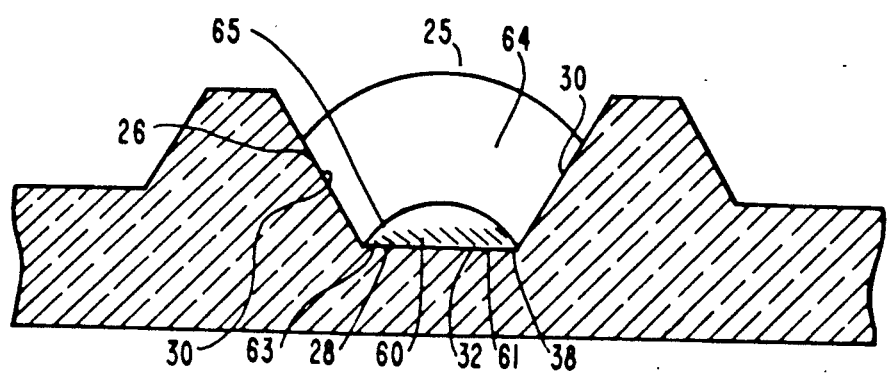
FIG. 7 is a section of the tray of FIG. 1. through one of the wells where the tray is preformed with a reagent.

In accordance with another embodiment of this invention, illustrated in FIG. 7, the tray can be preformed after rendering the surface 30 of the side wall 26 hydrophobic with the surface 32 of the bottom wall hydrophilic in the manner described above. The preformed trays are designed for a particular use. In such cases, the inner surface 32 of the bottom wall 28 of each of the wells 25 can be filled with a layer which contains an immunological component of the immunological antibody-antigen reaction in an aqueous medium. This aqueous layer 60 is placed in each well 25 so that its lower surface 61 contacts the inner surface 32 of the bottom wall 28. The precise antigen or antibody that is contained in this aqueous layer 60 will depend upon the antibody or antigen to be detected in the biological fluid, as well as whether the immunological reaction will either be a sandwich type immunological reaction or a competitive immunoassay. If it is desired to have a sandwich type immunoassay, the aqueous layer 60 will be the anti-sera to the antibody or antigen that is to be determined. In certain competitive assays, the aqueous layer 60 will contain the same antigen or antibody that is to be detected.

Placed in well 25 is a second layer 64 which is an inert a non-aqueous layer for preventing evaporation of the first layer 60. For the second layer any conventional non-aqueous viscous fluid which is non-miscible with water can be utilized. The fluid which forms layer 64 while preventing evaporation of the aqueous layer 60 should be permeable for aqueous mediums to allow passage of aqueous reagents placed into the well 25 so that these reagents will mix with the aqueous layer 60. Layer 64 is placed into well 25 so that the bottom surface 65 of layer 64 contacts and covers upper surface 63 of layer 60. The trays of FIG. 7 containing layers 60 and 64 represent preformed trays which are ready for carrying out the immunological reaction with the test fluid. In this manner, these trays are formed with the desired antigen to be detected or the antibody to this antigen in layer 60 and sold to the individual or group who wish to conduct the particular test with a sample of biological fluid.

For the HLA assay, it is preferred that 1 microliter of an individual HLA anti-serum be loaded into each well as the first layer 60 and be overlayed with 5 to 8 microliters of mineral oil, which prevents evaporation of the HLA anti-serum. In the testing procedure, the biological fluid containing isolated cells to be evaluated are then added to the various reaction wells and incubated. Following this incubation, rabbit complement reagent is added and also allowed to incubate. Rabbit compliment is a standard lysating agent for cells sensitized through immunological reaction with an antibody to these cells. Rabbit compliment will induce cytolysis or death of those cells in the biological fluid to which specific HLA antibodies in the anti-serum have attached by an immunological reaction. By so attaching cell death occurs. This cell death "positive reaction" is then determined for each well. After incubation with rabbit compliment, a dye or stain is added to the wells, which dye will penetrate the membranes of the dead cells. The tray is placed upon microscope and each well is visually observed for the uptake of stain. Uptake of stain by a cell indicates a "positive reaction". The HLA-phenotype of the cells to be analized is interpreted by using different specific HLA-antibodies in each or several of the wells in a plate and determining the positive reactions of the cells with each of the different specific antibodies. As seen from FIG. 1, each of the wells 25 are labeled horizontally by numbers and vertically by letters. Therefore, each well bears a specific number, letter and name and therefore, readings of each well can be referred to by a specific number letter relationship such as (11B).

It has been found that the use of the trays of this invention provides efficient mechanism for reading the wells. The use of hydrophilic bottom walls eliminates the formation of air bubbles in these wells, which formation prevents accurate readings.

EXAMPLE 1

Shielded Treatment Process for Plastic Trays

The plastic trays, were produced from hydrophobic polystyrene polymer.

A shield was made of a polymerized rubber replica casting product. The product consists of a base material and a catalyst which are mixed together in approximately equal volumes prior to use. This product has the property of practically zero shrinkage making it an excellent casting material.

To produce shields which would fit the trays exact to give maximum shielding to the wells, we designed a casting form. The casting form consists of a steel block with holes (approximately 0.067 inches in diameter) arranged geometrically such that they correspond exactly to the arrangement of the wells in the plastic tray. A plastic tray with holes (approximately 0.067 inch in diameter) drilled in the bottom of each well was placed over the steel block such that the holes in the tray and block were aligned. Steel rods (approximately 0.066 inch in diameter) were then pressed through each hole in the tray and steel block. This assembly allowed the rubber polymer product mentioned above to be poured directly into the casting mold. The rubber polymer in liquid state had the exact shape of the trays interior, including the wells, while the steel rods prevent the center of the wells to be filled. When the casting material polymerized and set, it was removed from the mold.

Shields were placed in untreated plastic trays. The shield covered the interior of the tray, including the sides of the wells completely, while allowing the bottom of the wells to be exposed. Following placement of the shields, the trays were treated with a corona arc discharge machine operating at 130 watts using a conveyor belt speed 7 ft. per minute. Basically, this machine consists of a variable speed conveyor belt system that allowed the tray to pass between an electrode assembly where the surface oxidation process takes place. The shield effectively blocked the treatment Process from all but the bottom of the tray wells. After treatment, the shields were removed from the trays. The trays were then destaticized and packaged until needed.

In evaluating the effect of this shielded treatment process, commercially available trays were compared with the tray prepared above. The wells of each tray were "loaded" with approximately five (5) $\mu$l of a light mineral oil. One (1) $\mu$l of an aqueous solution (approximately 0.5% buffered phenol red) was piped directly into the center of each well allowing the micro-drop to fall through the mineral oil and spread onto the bottom of the well. The aqueous solution spread relatively evenly across the bottom of the wells in all samples tested. The tray prepared with the rubber shield performed at improved level in this evaluation.

The next evaluation step was designed to test the shielded tray against currently available products when the aqueous reagent addition steps. (Due the extremely small drop formed by only one (1) $\mu$l of reagent.) In this evaluation step, one (1) $\mu$l of the above mentioned aqueous reagent was piped onto the side of the wells in each sample. On each commercially available tray sample, the micro-drop clung to the side of the well and remained there. (This would not allow the reagent to mix with any other reagents already present in the tray well bottom or added later!) When the micro-drop was added to the shielded treatment tray of this invention, the droplet immediately rolled down the side of the well and spread evenly across the bottom of the well. This effect was repeated on subsequent trials.

EXAMPLE 2

Use of Treated Plastic HLA Tray

The treated plastic HLA tray of Example 2 was used in producing pre-filled HLA tissue typing reagent trays. These reagent trays determine HLA antigens which may be present on the surface of leukocytes. The following procedure for the production of such reagent trays was used:

Approximately four (4) to ten (10) microliters of mineral oil was placed into each well of a treated plastic HLA tray. Next, one (1) microliter of a specific HLA antiserum was added to each well such that it underlayed the mineral oil and spread across the well bottom. The filled tray was now ready for use in an HLA phenotyping assay, or it may be stored frozen (i.e. $-70°$ C.) until needed.

EXAMPLE 3

Use of Pre-filled HLA Tissue Typing Reagent Tray

Pre-filled HLA reagent trays are used to determine HLA antigens which may be present on lymphocytes. In such determinations, the following procedure was utilized.

All lymphocytes express the HLA class I antigens for the A, B, and C loci. Lymphocytes were readily isolated from whole blood by several methods. The method described herein was designed to produce a yield of viable lymphocytes which is at least 90% in purity. These isolated lymphocytes were then utilized in standard lymphocytotoxicity procedures to determine specific HLA antigens which may be present on the cell membrane.

Anticoagulants most commonly used for HLA sample collection were sodium heparin and acid citrate dextrose. The following procedure utilizes sodium heparin as the anticoagulant. For optimum cell purity and viability, blood samples were stored at room temperature and processed within twenty-four (24) hours of collection. Lymphocyte viability begins deteriorating rapidly after twenty-four (24) hours.

Materials

1.) 3 ml whole blood (sodium heparin anticoagulant)
2.) 16×125 mm test tubes
3.) 12×75 conical centrifuge tubes
4.) Pasteur pipets
5.) 3% gelatin in 0.9% saline (175 bloom gelatin)
6.) Hot 0.9% saline (approximately 56° C.)
7.) Nylon wool column
   * Pack a 10 ml syringe with approximately 1 gram of scrubbed nylon wool to a height of about 2 cm. Place a 20 gauge needle on the end of the syringe to act as a flow restriction device.
8.) Ficoll-Hypaque cell separation media
   * specific gravity 1.077
9.) RPMI cell culture media
10.) 37° C. water bath
11.) Centrifuge (swinging buckets)
   * capable of 800 RCF
12.) Hemacytometer
13.) Capillary tubes
14.) Brightfield microscope
15.) Micro-pipets
   * 1 µl, 2 µl, and 5 µl delivery
16.) Pre-filled HLA tissue typing reagent tray
17.) Rabbit complement
18.) 5% Eosin-Y soln.
19.) 7% buffered Formalin soln. (pH. approx. 7.2)
20.) HLA tray cover slip
21.) Phase contrast inverted microscope

Procedure

Pour off approximately 3 ml of whole blood into a 16×125 test tube. Add 10 ml of 3% gelatin soln. (37° C.) and mix gently. Place the mixture in a 37° C. water bath and allow the red cells to settle out for about 15–20 minutes.

After the 15–20 minute incubation, place a prepared nylon wool column into a 16×125 mm test tube and fill with hot 0.9% saline. Allow the hot saline to drain through the column. When the hot saline has finished draining from the column, place the column into another 16×125 mm test tube at an angle such that the needle touches the inside wall of the test tube. Immediately remove the supernatant from the incubating blood/gelatin mixture with a Pasteur pipet and allow it to drain through the mylon wool column and into the test tube. As soon as the supernatant has filtered through the column, place the column into another 16×125 mm test tube which contains 3 ml of Ficoll-Hypaque cell separation media. Place the column at a slant as mentioned above such that the needle rests against the inside of the test tube. Pour the supernatant back through the column for a second filtration allowing the filtrate to run down the inside of the test tube and layer onto the separation media.

Once the sample has finished layering on the separation media, sample was placed into the centrifuge being careful not to disturb the layer interface. The layered supernatant was centrifuged at 800 RCF for 20 minutes. The sample was removed from the centrifuge being careful not to disturb the interface.

An opaque buffy coat layer formed directly above the separation media which contains primarily lymphocytes and platelets. Using a Pasteur pipet, carefully remove this buffy coat from the separation media and place it into a 12×75 conical centrifuge tube. (Take caution to avoid picking up excessive amounts of sample above or below this buffy coat.)

The buffy coat was diluted in the 12×75 tube with RPMI cell culture media, mix gently, and centrifuge at 200 RCF for ten (10) minutes. This step was designed to remove remaining separation media as well as begin removing platelets. Decant the platelet rich supernatant after centrifugation and resuspend the lymphocyte rich pellet in the bottom of the tube. Dilute the pellet with RPMI media, mix gently, and centrifuge at 200 RCF for five (5) minutes. Decant the supernatant, resuspend the pellet, mix gently, and centrifuge again at 200 RCF for five (5) minutes. The last two wash steps should remove most remaining platelets.

Following the last wash step, resuspend the cell pellet in a minimal amount of RPMI media. Observe the cell suspension on a hemacytometer under brightfield microscopy for lymphocyte purity and concentration. Wash the suspension again if necessary to remove excess platelets. The final lymphocyte suspension should be adjusted with RPMI media to a concentration of 1000–2000 lymphocytes/1 µl.

When the cells have been properly adjusted, they are ready to "plate" onto a pre-filled HLA tissue typing reagent tray. Using a micro-pipet, add one (1) µl of mixed cell suspension to each well of the typing tray. Incubate the "plated" tray for thirty (30) minutes at room temperature. After this incubation, add five (5) µl of rabbit complement to each well and incubate for sixty (60) minutes at room temperature. Following this incubation, add two (2) µl of 5% Eosin-Y solution to each well and incubate for five (5) minutes at room temperature. When this incubation has finished, add five (5) µl of 7% buffered formalin solution. Allow the plate to sit undisturbed for about two (2) hours at room temperature. (Plates may be stored in a humidity chamber if they are to be left longer than 2 hours.)

Place a cover slip over the reagent tray wells being careful not to entrap air bubbles in the wells. Observe the wells for cytotoxicity using an inverted phase contrast microscope. Dead cells will appear dark while live cells remain translucent. Specific antigen presence on the membrane is indicated by cytotoxic reactions with corresponding antisera.

I claim:

1. A tray for conducting immunogenic reactions for analyzing biological fluid samples comprising a plate member having top and bottom surfaces with the top surface of said plate member defining a plurality of spaced-apart wells configured and adapted to receive and hold the biological fluid for conducting the immunogenic reaction, said wells having a side and bottom walls with inner surfaces, the inner surfaces of said wells being adapted to retain said fluid, said inner surface of side wall being hydrophobic and said inner surface of said bottom wall being hydrophilic.

2. The tray of claim 1 wherein the bottom walls of the respective wells define a surface area, and said wells include an upper rim on said top surface which define a surface area greater than the surface area defined by said bottom walls.

* * * * *